US008846353B2

(12) United States Patent
Tsobanakis et al.

(10) Patent No.: US 8,846,353 B2
(45) Date of Patent: Sep. 30, 2014

(54) METHODS OF MANUFACTURING ACRYLIC ACID

(71) Applicant: Cargill, Incorporated, Wayzata, MN (US)

(72) Inventors: Paraskevas Tsobanakis, Mendota Heights, MN (US); Xiangsheng Meng, Troy, OH (US); Timothy Walter Abraham, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 13/719,095

(22) Filed: Dec. 18, 2012

(65) Prior Publication Data

US 2013/0150616 A1   Jun. 13, 2013

Related U.S. Application Data

(60) Continuation of application No. 12/507,008, filed on Jul. 21, 2009, now Pat. No. 8,338,145, which is a division of application No. 10/509,183, filed as application No. PCT/US03/09095 on Mar. 25, 2003, now abandoned.

(60) Provisional application No. 60/367,301, filed on Mar. 25, 2002.

(51) Int. Cl.
*C12P 7/62* (2006.01)

(52) U.S. Cl.
USPC .......................................... 435/135; 560/179

(58) Field of Classification Search
USPC .......................................... 435/135; 560/179
See application file for complete search history.

(56) References Cited

U.S. PATENT DOCUMENTS

| | | | |
|---|---|---|---|
| 2,379,625 A | 7/1945 | Coes, Jr. | |
| 2,469,701 A | 5/1949 | Redmon | |
| 2,859,240 A | 11/1958 | Holmen | |
| 3,590,073 A | 6/1971 | Carr et al. | |
| 3,619,397 A | 11/1971 | Jacquemet | |
| 3,639,466 A * | 2/1972 | Leichtle | 562/599 |
| 3,954,854 A * | 5/1976 | Gehrmann et al. | 562/599 |
| 4,187,300 A | 2/1980 | Kinnamon | |
| 4,211,846 A | 7/1980 | Lafferty | |
| 4,729,978 A * | 3/1988 | Sawicki | 502/174 |
| 4,786,756 A | 11/1988 | Paparizos et al. | |
| 4,937,359 A | 6/1990 | Seebach et al. | |
| 4,970,334 A | 11/1990 | Argyropoulos et al. | |
| 5,132,456 A * | 7/1992 | King et al. | 562/593 |
| 5,294,720 A | 3/1994 | Jadhav et al. | |
| 5,439,674 A | 8/1995 | Noda et al. | |
| 5,659,029 A | 8/1997 | Ellis et al. | |
| 7,186,541 B2 | 3/2007 | Gokarn et al. | |
| 8,338,145 B2 | 12/2012 | Tsobanakis et al. | |
| 2001/0008736 A1 | 7/2001 | Fanta et al. | |
| 2005/0221457 A1 | 10/2005 | Tsobanakis et al. | |
| 2005/0222458 A1 * | 10/2005 | Craciun et al. | 562/599 |
| 2009/0298144 A1 | 12/2009 | Tsobanakis et al. | |
| 2010/0273224 A1 | 10/2010 | Joachim et al. | |

FOREIGN PATENT DOCUMENTS

| | | |
|---|---|---|
| DE | 3222837 | 12/1983 |
| JP | 53-18794 | 2/1978 |
| JP | 58-158189 | 9/1983 |
| JP | 61-115049 | 6/1986 |
| JP | 63313739 A | 12/1988 |
| JP | 09-143126 | 6/1997 |
| JP | 2002-053524 | 2/2002 |
| WO | WO01/16346 | 3/2001 |
| WO | WO02/090312 | 11/2002 |

OTHER PUBLICATIONS

Lira et al. Ind. Eng. Chem. Res. (1993) 32: 2608-2613.*
Notice of Reasons for Rejection, mailed Oct. 23, 2012, issued in corresponding JP 2009-188539 (with English-language translation).
Notice of Reasons for Rejection from the Japanese Patent Office for Japanese Patent Application No. 2009-188539, dated Mar. 27, 2012 (with translation).
Aldrich Chemical Co., Inc., Catalog, p. 961 (1996).
Bartoli et al., "An efficient procedure for the diasteroselective dehydration of beta-dydroxy carbonyl compounds by CeCl (3).7H(2)O/Nal System," *Organic Lett.*, vol. 2, No. 13, pp. 1791-1793 (Jun. 2000).
Chattopadhyay et al., "Enzymatic Esterification of 3-Hydroxybutyric Acid," *Biotechnology Letters*, vol. 15, No. 3, pp. 245-250 (Mar. 1993).
Drushel, W.A. et al., "Über die Darstellung and Eigenschaften der Hydracrylsäureester," *Chemisches Zentralblatt*, vol. 87, pp. 142-143 (1916), XP008019488 XX, XX, p. 142-143, paragraph 3—paragraph 2.
English abstract for JP363313739 downloaded from Derwent on Apr. 20, 2009.
Final Office Action for related Japanese Patent Application No. 2003-580264, dated Dec. 21, 2010.
Fischer, Emil, "Zur Kenntnis der VValdenschen Umkehrung IV," *Chemische Berichte*, vol. 42, pp. 1219-1228 (Mar. 1909), XP001149222 Verlag Chemie GmbH. Weinheim., DE ISSN: 0009-2940, p. 1221, paragraph 3.
From et al., "Lipase catalyzed esterification of lactic acid," *Biotechnology Letters*, vol. 19, No. 4, pp. 135-134 (Apr. 1997).
Hasegawa, J. et al., "Production of beta-Hydroxypropionic Acid from Propionic Acid," *Journal of Fermentation Technology*, vol. 60, No. 6, pp. 591-594 (Dec. 1982), XP008019541 Tokyo, JP, p. 594, left-hand column.
Kissa, "Solubility of Alkali Metal Carboxylates in Hydrocarbons," *Journal of Colloid Science*, vol. 17, No. 9, pp. 857-864 (Dec. 1962).
Levene et al., "The Configurational Relationships of 2-Hydroxy, 3-Hydroxy and 4-Hydroxy Acids," *Journal of Biological Chemistry*, vol. 69, pp. 165-173 (Apr. 1926), XP008019487 American Society of Biological Chemists, Baltimore, MD., US ISSN: 0021-9258, p. 167.

(Continued)

*Primary Examiner* — Susan Hanley

(57) ABSTRACT

Preparation of derivatives of β-hydroxycarboxylic acid, including β-hydroxycarboxylic acid esters, α,β-unsaturated carboxylic acid, esters of α,β-unsaturated carboxylic acid, and alkoxy derivatives, such as preparation of acrylic acid from 3-hydroxypropionic acid.

21 Claims, No Drawings

(56) References Cited

OTHER PUBLICATIONS

Notice of Reasons for Rejection from the Japanese Patent Office for Japanese Patent Application No. 2003-580264, dated Jan. 19, 2010 (with translation).

Notification (with English-language translation) from the Japanese Patent Office for Japanese Patent Application No. 2003-580264, mailed Nov. 2, 2010.

Office Action from the U.S. Patent and Trademark Office for U.S. Appl. No. 12/507,008, mailed Nov. 15, 2011.

Office Action from the U.S. Patent and Trademark Office for U.S. Appl. No. 12/507,008, mailed May 22, 2012.

Riemenschneider, W.: "Ullmann's Encyclopedia of Industrial Chemistry, Sixth Edition, 1999 Electronic Release," 1999, Wiley-VCH, Weinheim, Germany, XP002247378 Esters, Organic-Production.

Seo et al., "Kinetics of Esterification of Lactic Acid with Methanol in the Presence of Cation Exchange Resin Using a Pseudo-Homogeneous Model," *Journal of Chemical Engineering of Japan*, vol. 33, No. 1, pp. 128-133 (No month available, 2000).

van der Baan et al., "Synthesis of β-Hydroxy Esters by Lithium/Ammonia Rejection of α,β-Epoxy Esters," *Synthesis*, vol. 10, pp. 897-899 (Oct. 1990).

Ullman's Encyclopedia of Industrial Chemistry, 5th edition, 1994, pp. 181, 196 and 199.

Odell et al., "Hydrothermal Reactions of Lactic Acid Catalysed by Group VIII Metal Complexes," J Organomet Chem. 1985, vol. 290, pp. 241-248.

Morrison et al., "Organic Chemistry," vol. 1, Fourth edition, 1983, p. 423.

\* cited by examiner

METHODS OF MANUFACTURING ACRYLIC ACID

STATEMENT OF RELATED CASES

This is a Continuation of U.S. patent application Ser. No. 12/507,008, filed Jul. 21, 2009, now U.S. Pat. No. 8,338,145, which is a Divisional of U.S. patent application Ser. No. 10/509,183, filed May 19, 2005, now abandoned, which is the U.S. National Stage of International Application No. PCT/US03/09095, filed Mar. 25, 2003, which was published in English under PCT Article 21(2), which in turn claims the benefit of U.S. Provisional Application No. 60/367,301, filed Mar. 25, 2002, which are all incorporated herein in their entirety.

TECHNICAL FIELD

This invention relates to preparing derivatives of β-hydroxycarboxylic acids.

BACKGROUND

Hydroxycarboxylic acids (HCA's) are an especially interesting and useful class of compounds. They are, by their very nature, bifunctional and therefore allow for a multitude of chemical transformations. Both functional groups, i.e., the hydroxy and the carboxylic acid groups, can, under certain conditions, react independently of one another, thereby generating the classical derivatives of each group, yet at other times may interact with each other to perturb their normal chemical reactivities. Also of interest is the possibility for reaction between the two functional groups leading to dimeric, oligomeric, and, importantly, polymeric materials. In the case of beta-hydroxycarboxylic acids (β-HCA's), there is also the possibility of dehydration via loss of the hydroxy group and an adjacent hydrogen atom. Such dehydration can lead to the formation of alpha, beta-unsaturated carboxylic acids, an important class of compounds in their own right.

Two very common and commercially important alpha, beta-unsaturated carboxylic acids are the acrylate and methacrylate families. Acrylic acid, salts of acrylic acid, and esters of acrylic acid are used in the manufacture of polyacrylic acid, polyacrylic acid salts, and polyacrylates. These materials are useful as surface coatings, adhesives and sealants, absorbents, textile and non-wovens, and plastic modifiers.

SUMMARY

Methods of preparing derivatives of β-HCA's and their salts are provided. The derivatives include esters (particularly "light" esters made by reacting the acid with a $C_1$-$C_7$ alcohol), α,β-unsaturated carboxylic acids and esters (e.g., acrylic acid and acrylate esters), and alkoxy derivatives prepared by reacting the β-HCA with an alcohol. These derivatives, in turn, may be subjected to further processing. For example, the β-HCA esters may be hydrogenated to form polyols.

The β-HCA may be derived from a biomass fermentation broth. The term "alcohol" includes both monofunctional alcohols (i.e., alcohols having one hydroxyl group) and polyfunctional alcohols (i.e., alcohols having two or more hydroxyl groups).

The details of one or more embodiments of the invention are set forth in the description below. Other features, objects, and advantages of the invention will be apparent from the description and from the claims.

DETAILED DESCRIPTION OF EMBODIMENTS

Methods are described for producing derivatives of β-HCA's, including, for example, esters of β-HCA's, acrylic acid, salts of acrylic acid, esters of acrylic acid, and alkoxy derivatives. The β-HCAs useful in preparing these derivatives include, for example, 3-hydroxypropionic acid, 3-hydroxy-2-methylpropionic acid, 3-hydroxybutanoic acid, 3-hydroxy-2-methylbutanoic acid, 3-hydroxy-2-methylpentanoic acid, 3-hydroxy-3-methylbutanoic acid, 2,3-dimethyl-3-hydroxybutanoic acid, 3-hydroxy-3-phenylpropionic acid, and combinations thereof. These β-HCAs, and their salts, can be obtained from a variety of sources. Useful sources of β-HCA's and salts thereof include fermentation and enzymatic processes. The fermentation reaction that produces the acid typically involves the fermentation of a sugar in the presence of a micro-organism such as what has been described in U.S. Patent Application 60/285,478 filed on Apr. 20, 2001. The β-HCA and/or its salt are then separated from the fermentation broth. This can be accomplished using various techniques, including, for example an extractive salt-splitting method as described in PCT Application No. US02/14315 (published as WO 02/090312), entitled "Process for Preparing Carboxylic Acids and Derivatives Thereof." As described therein, a process for preparing a hydroxyl-functional carboxylic acid can use ammonia or an amine to neutralize the acid, thereby forming an ammonium salt of the acid. The ammonium salt of the carboxylic acid can then be separated from the fermentation broth by adding an organic extractant and heating the mixture to split the ammonium salt and partition the acid into the organic solvent. The resultant organic composition, therefore, includes, among other things, the acid with the organic extractant. The acid-organic extractant combination can be separated from the remaining aqueous fermentation broth and back extracted to separate the extractant from the acid, thereby producing the pure (i.e. free) acid.

A discussion of the preparation of specific derivatives follows.

Esters of β-HCA's

Certain methods according to the invention can be used to prepare a carboxylic acid ester of β-HCAs or salts thereof under relatively mild conditions. The esterification process is facilitated by reacting the β-HCA, or salt thereof, with an alcohol, and can be accomplished in the presence of an esterification catalyst and the absence of a solvent other than the alcohol. Alternatively, a carboxylic acid ester can be prepared by reacting a β-HCA, or salt thereof, with a light alcohol having between 1 and 7 carbon atoms, inclusive, in the presence of a water immiscible extractant and an optional esterification catalyst. This technique is particularly useful when the β-HCA is derived from a fermentation broth via extractive salt splitting using an organic extractant. Allowing the β-HCA to react with the alcohol in the presence of an esterification catalyst in the extractant produces a mixture that includes the ester and the extractant.

Exemplary extractants include amides, ethers, ketones, phosphorus esters (e.g., tributyl phosphate), phosphine oxides, phosphine sulfides, and alkyl sulfides. Any of these extractants can be used alone or in combination with another.

The reaction is conducted under conditions that favor esterification over dehydration. Esterification can proceed when the reaction takes place in substantially anhydrous conditions at atmospheric pressure and a temperature less than reflux temperature to produce the ester. Preferably, the reaction is conducted at ambient temperature.

Alcohols useful in preparing an ester are those that are miscible or partially miscible with water. Suitable alcohols include, for example, $C_1$ to $C_{26}$ alcohols, including straight chained, branched, and cyclic organic moieties. These moieties can be aliphatic, aromatic or combinations thereof. Light or primary alcohols (e.g., those containing between 1 and 7 carbon atoms, inclusive) ranging from methanol to heptanol are particularly useful. The alcohols can be straight chained or branched and either primary, secondary or tertiary. In addition, the alcohols can be monofunctional (i.e., containing a single hydroxyl group) or polyfunctional (i.e. containing two or more hydroxyl groups). Examples of polyfunctional alcohols include glycols and polyols such as glycerol, 1,2-ethanediol (ethylene glycol), 1,3-propanediol, 1,4-butanediol, 1,2-propanediol, and polyoxyethylene (PEO or PEG) derivatives thereof.

A distillation step can be performed after the addition of the alcohol to an aqueous composition containing the β-HCA. This can be conducted by distilling off a water-containing distillate until the residual β-HCA/alcohol mixture is substantially dry. In one technique, an azeotropic distillation with an organic solvent such as toluene can be performed. Optionally, the alcohol used in the esterification of the β-HCA can also be included in the distillation step.

Upon achieving a substantially anhydrous condition, an esterification catalyst can subsequently be added to induce esterification. Suitable esterification catalysts for the process include acidic resins, acidic inorganic salts, and mineral acids. Useful mineral acids include acids such as sulfuric or phosphoric acid. Inorganic salts such as anhydrous copper sulfate can be used. Exemplary acid resin catalysts include commercially available compounds such as acidic AMBERLYST® resins (available from Rohm and Haas Co.; Philadelphia, Pa.), NAFION™ resins (available from E.I. DuPont de Nemours and Co.; Wilmington Del.), and acidic DOWEX™ resins (available from Dow Chemical Co.; Midland, Mich.). An acidic resin can be used in a form that allows contact of the acidic resin with vapors or liquid of the β-HCA. For example, the resin may be in the form of a bed or column.

Purification of the desired ester product can be achieved by distillation. Yields for the ester using certain methods of the invention can be greater than about 80%.

α/β-Unsaturated Carboxylic Acids and Salts Thereof

Dehydration of a β-HCA can provide α,β-unsaturated carboxylic products. In an exemplary method, an α,β-unsaturated carboxylic acid or salt thereof can be prepared by heating an aqueous solution having a β-HCA salt to dehydrate the salt and form the α,β-unsaturated carboxylic acid and/or a salt thereof. The aqueous solution can be derived from a fermentation broth or other enzymatic process. One advantage of this process is that while the β-HCA salts are water-soluble, the corresponding salts of the α,β-unsaturated carboxylic acid generally are not. Thus, the salts of the α,β-unsaturated carboxylic acid precipitate out of solution, thereby facilitating separation of the unsaturated acid from the starting material.

The salt of the β-HCA can be any one of an alkali metal salt, an alkaline earth salt, or combination thereof. Typical salts include, for example, sodium and calcium salts. Dehydration to produce an α,β-unsaturated carboxylic acid or a salt thereof can occur in aqueous media since the β-HCA is soluble in aqueous solutions.

Optionally, a dehydration catalyst can be added to the aqueous solution as it is heated to enhance dehydration of the acid or acid salt to form an α,β-unsaturated carboxylic acid or a salt thereof. Acidic or basic materials can be used to catalyze the dehydration process in the aqueous media. A dehydration catalyst can be neutral, acid, or base materials that facilitate dehydration. Examples of neutral catalysts include for example, calcium phosphate, calcium lactate, and calcium 3-hydroxypropionate. Other useful catalysts include aluminum oxide, silicon oxide, titanium oxide, zirconium oxide, zeolites, and other Lewis acids. Amines are basic compounds that can be used as a catalyst. Where a fermentation broth is used to provide the β-HCA, a basic amine can conveniently function both as the extractant to separate the β-HCA from the aqueous fermentation broth as well as a dehydration catalyst. Exemplary amines suitable for the process include tricapryl amine (TCA), tridecyl amine (TDA), and tridodecyl amine (TDDA). Still other exogenous basic materials can be utilized to effect dehydration. In particular, metal oxides and hydroxides such as calcium oxide and calcium hydroxide are basic materials that can enhance and assist dehydration. Acid catalysts can be strong mineral acids such as hydrochloric, sulfuric, or phosphoric acids in their gaseous or liquid form. Insoluble acid resins such as acidic AMBERLYST® resins, NAFION™ resins, and acidic DOWEX™ resins, for example, can also be employed as catalysts. A particularly useful acid catalyst is phosphoric acid.

An α,β-unsaturated carboxylic acid can also be prepared by dehydration conducted by vapor-conversion (i.e. vapor phase reaction). In such methods, an aqueous solution having a β-HCA can be vaporized at relatively high temperature, preferably in the presence of a dehydration catalyst, to convert the β-HCA into an α,β-unsaturated carboxylic acid.

α/β-Unsaturated Carboxylic Acid Esters

Process conditions that drive an esterification process of β-HCAs can also drive the dehydration of these materials, using elevated temperatures and acid or base catalysis. Similarly, esterification of an α,β-unsaturated carboxylic acid can also be achieved using elevated temperatures, and acid or base catalysis. Thus, in an exemplary method, both esterification and dehydration processes of α,β-unsaturated carboxylic acid can be conducted within the same reaction vessel.

Different pathways are available for preparing an ester of α,β-unsaturated carboxylic acid. In one route, a β-HCA, or an ammonium salt thereof, is initially esterified via reaction with an alcohol. A subsequent dehydration of the ester can then be conducted to provide an ester of α,β-unsaturated carboxylic acid. In an alternative path, β-HCA is initially dehydrated, after which the resulting α,β-unsaturated carboxylic acid or a salt thereof is esterified using an alcohol to yield an ester of the α,β-unsaturated carboxylic acid.

In aqueous media, an α,β-unsaturated carboxylic acid ester can be prepared by initially converting a β-HCA or a salt thereof to an ester; thereafter, the solution having the ester and a dehydration catalyst can be vaporized to convert the β-HCA ester to an α,β-unsaturated carboxylic acid ester.

Alkoxy Derivatives

By heating an aqueous solution containing a β-HCA or salt thereof and an alcohol in a closed reactor, it is possible to produce a variety of derivatives, including, for example, α,β-unsaturated carboxylic acid esters, α,β-unsaturated carboxylic acids, β-alkoxy carboxylic acids or esters. To achieve the esters, it can be advantageous to add an esterification catalyst to the solution. As with other processes described herein, the β-HCA, or salt thereof, can be in an aqueous solution derived from, for example, a fermentation broth.

An alkoxy derivative of a β-HCA can be prepared by reacting an aqueous solution having a β-HCA or a salt thereof with alcohol, in the presence of a basic catalyst in a closed reactor such as a Parr reactor. The solution can be heated to allow the reaction to form an alkoxy derivative of the acid. The basic catalyst can be any one of $Mg(OH)_2$, $Ca(OH)_2$, NaOH, or combinations thereof.

EXAMPLES

All percentages are weight percentages unless otherwise noted.

The products of the reactions described below were analyzed using High Performance Liquid Chromatography (HPLC) and Gas Chromatography (GC).

The equipment used in the HPLC analyses included a Waters 1525 binary HPLC pump equipped with a Waters 717 plus Autosampler, and Waters 2410 Refractive Index and 2487 Dual Lambda Absorbance Detectors. A Bio-Rad HP87-H column was used. The mobile phase was 0.004 N sulfuric acid. The flow rate was 0.6 mL/min. and the column temperature was 60° C.

The equipment used in the GC analyses included a J&W DB-WAXETR 30 m×32 mm, 0.5 μm film column. The initial oven temperature was 90° C. with a 20° C./min. increase to a final temperature of 200° C. The sample was maintained at the final temperature for about 12.5 minutes. The injector temperature was 200° C.

Example 1

This example describes the resin acid-catalyzed conversion of 3-HP to various alkyl esters. The 3-HP was in the form of a 30% aqueous solution. 70% of the material was pure 3-HP monomer.

20.65 g of 30% 3-HP was dried by azeotropic distillation with methanol. To the dried 3-HP was added an excess (56.84 g) of anhydrous methanol, and 5.05 g of dry AMBERLYST-15. The mixture was stirred at room temperature for 18 hrs and monitored by GC.

There were two main peaks in the chromatogram, at 5.13 min. and 7.89 min., corresponding to the methyl ester of 3-HP and the dimethyl ester of the ether dimer of 3-HP, respectively. The 3-HP that is used in the reaction is only about 70% pure monomer, the rest being dimers and a trace of acrylic acid. The identity of the 3-HP methyl ester was confirmed by GC-MS.

At the end of the reaction, the solid catalyst was filtered off, and the solvent removed by vacuum distillation. The crude product was subjected to flash column chromatography in order to obtain pure material. A calibration curve was generated on the GC for the ester.

The above reaction was repeated using 3.18 g of 30% 3-HP, 15.88 g of dry methanol, and 1.02 g of AMBERLYST-15. The reaction mixture was stirred at room temperature for 21 hours and monitored by GC. The calibration curve from the above experiment was used to determine the yield.

| Time | Yield* |
|---|---|
| 4 hrs | 70% |
| 21 hrs | 100% |

*Based upon 70% purity of 3-HP

The above reaction was repeated using 3.14 g of 30% 3-HP, 17.47 g of dry ethanol, and 1.12 g of dry AMBERLYST-15 to prepare the ethyl ester of 3-HP. The reaction mixture was stirred at room temperature for 19 hrs and monitored by GC.

| Time | Yield* |
|---|---|
| 2.5 hrs | 17% |
| 19 hrs | 68% |

*Based upon 70% purity of 3-HP

The above reaction was repeated except that butanol was used as the alcohol. After 19 hours, the yield of butyl ester was 70%, based upon 70% purity of the 3-HP starting material.

The above reaction was repeated except that 2-ethylhexyl alcohol was used as the alcohol. After 19 hours, the yield of 2-ethylhexyl ester was 59%, based upon 70% purity of the 3-HP starting material.

The above reaction was repeated except that NAFION NR-50, rather than AMBERLYST-15, was used as the catalyst. The alcohol was ethanol. The mixture was stirred at room temperature for 21 hours, and monitored by GC. The yield of 3-HP ethyl ester was 71%, based upon 70% purity of the 3-HP starting material.

Example 2

This example describes the synthesis of the methyl ester of 3-HP at room temperature using $H_2SO_4$ as the catalyst. The 3-HP was in the form of a 30% aqueous solution. 70% of the material was pure 3-HP monomer.

30% aqueous 3-HP was dried by azeotropic distillation with methanol. To the dried 3-HP was added excess methanol and a few drops of conc. $H_2SO_4$. The mixture was stirred at room temperature for 24 hrs, while being monitored by GC. After 24 hrs of stirring, most of the 3-HP had been converted to the ester.

| Time | Yield* |
|---|---|
| 3.5 hrs | 89% |
| 6 hrs | 92% |
| 24 hrs | 96% |

*Based upon 70% purity of 3-HP

Example 3

This example describes the conversion of 3-HP to it methyl ester using an acid resin catalyst. The 3-HP was in the form of a 14.72% aqueous solution. 98.7% of the material was pure 3-HP monomer.

16.685 g of 14.72% aqueous 3-HP (25.7 mmol) was dried by removing the water on a rotary evaporator. To the dried 3-HP (2.371 g) was added 16 g of methanol and 0.548 g of AMBERLYST-15 acid resin catalyst. The mixture was stirred at room temperature for 28 hrs and monitored by GC. Another 0.549 g of AMBERLYST-15 acid resin catalyst was then added and the mixture stirred for an additional 18 hrs to produce the methyl ester of 3-HP.

| Time | Yield* |
|---|---|
| 2 hrs | 31% |
| 4 hrs | 42% |
| 20 hrs | 81% |
| 28 hrs | 95% |
| 46 hrs | 100% |

*Based upon 98.7% purity of 3-HP

Example 4

This example describes the conversion of 3-HP to it methyl ester using $H_2SO_4$ as the catalyst. The 3-HP was in the form of a 14.72% aqueous solution. 98.7% of the material was pure 3-HP monomer.

18.524 g of 14.72% aqueous 3-HP (30.2 mmol) was dried by removing the water on a rotary evaporator. To the dried 3-HP (2.717 g) was added 13 g of methanol and 0.22 g of concentrated $H_2SO_4$ catalyst. The mixture was stirred at room temperature for 22 hrs and monitored by GC to produce the methyl ester of 3-HP.

| Time | Yield* |
|---|---|
| 1.5 hrs | 75% |
| 3.5 hrs | 88% |
| 22 hrs | 95% |

*Based upon 98.7% purity of 3-HP

Example 5

This example describes the preparation of calcium acrylate from the calcium salt of 3-HP.

A 56 g aqueous solution of the calcium salt of 3-HP, made from 5.22 g 30% 3-HP and 0.65 g $Ca(OH)_2$, was heated at 220° C. in a 600 ml Parr reactor for 2 hours. After cooling down to room temperature, the solution was analyzed by GC and HPLC for acrylic acid and 3-HP. The yield of and conversion to calcium acrylate from the calcium salt of 3-HP were 48.7% and 47.1%, respectively. This gave a 100% selectivity from the calcium salt of 3-hydroxypropionic acid to calcium acrylate. The carbon balance of the reaction was 101.7%.

Example 6

This example describes the preparation of sodium acrylate from the sodium salt of 3-HP.

A 21 g aqueous solution of the sodium salt of 3-HP, made from 5.027 g 30% 3-HP and 0.69 g NaOH, was heated at 220° C. in a Parr reactor for 2 hours. After cooling down to room temperature, the solution was analyzed by GC and HPLC for acrylic acid and 3-HP. The yield of and conversion to sodium acrylate from the sodium salt of 3-HP were 41.8% and 61.3%, respectively. This gave a 68.2% selectivity from the sodium salt of 3-HP to sodium acrylate. The carbon balance of the reaction was 80.6%.

Example 7

This example describes a vapor phase conversion of 3-HP to acrylic acid using a sulfuric acid catalyst.

0.8139 g of aqueous 30% 3-HP and 0.2800 g of concentrated $H_2SO_4$ (about 1:1 molar ratio) were mixed and immediately injected into a GC. The concentration of acrylic acid was determined using a calibration curve. The yield of acrylic acid was 97.8%. When the experiment was repeated, a yield of 99.97% acrylic acid was obtained. Similar experiments were conducted by changing the ratio of 3-HP to $H_2SO_4$; the results are shown in the following table.

| Ratio of 3-HP:$H_2SO_4$ | Concentration of 3-HP | % Yield of Acrylic acid |
|---|---|---|
| 4:1 | 7.7% | 100 |
| 9:1 | 7.7% | 76 |
| 19:1 | 7.7% | 66 |
| 8.5:1 | 30% | 94 |
| 15:1 | 30% | 81 |
| 19:1 | 30% | 75 |

Example 8

This example describes the vapor phase conversion of 3-HP to acrylic acid using a phosphoric acid catalyst.

0.5005 g of 7.117% 3-HP and 0.3525 g of 85% $H_3PO_4$ were mixed and immediately injected into a GC. In a second experiment, 0.5041 g of 7.117% 3-HP and 0.0505 g of 85% $H_3PO_4$ were used. The results are reported in the table, below.

| Amount of 3-HP | Amount of 85% $H_3PO_4$ | Molar ratio of 3-HP to $H_3PO_4$ | % Yield of Acrylic acid |
|---|---|---|---|
| 0.5005 g | 0.3525 g | ~1:8 | 82.6 |
| 0.5041 g | 0.0505 g | ~1:1 | 92.5 |

Example 9

This example describes the preparation of acrylic acid from 3-HP using a Cu—Ba—CrO catalyst.

50.0 g of 5.13% 3-HP was placed in a Parr reactor along with 0.50 g of Cu—Ba—CrO catalyst. The mixture was heated at 200° C., under 310 psi of nitrogen, for 22 hours. The reaction mixture was cooled to room temperature and analyzed by GC. The conversion of 3-HP was 63% and selectivity to acrylic acid was 100%.

Example 10

This example describes the vapor phase conversion of 3-hydroxyisobutyric acid (also known as 3-hydroxy-2-methylpropionic acid) to methacrylic acid using either a sulfuric acid or phosphoric acid catalyst.

A 15.5% aqueous solution of 3-hydroxyisobutyric acid (3-HIBA) was mixed with varying amounts of concentrated sulfuric acid and injected into a GC. One experiment was also performed with concentrated phosphoric acid. The results are reported in the table, below.

| Molar ratio of 3-HIBA:$H_2SO_4$ | % Conversion | % Selectivity |
|---|---|---|
| 0.9:1 | 94.7 | 94.4 |
| 1.6:1 | 92.6 | 97.6 |
| 1.5:1 | 94.2 | 92.3 |
| 2.4:1 | 91.7 | 90.7 |
| 4.5:1 | 87.0 | 83.7 |
| 11.2:1 | 72.2 | 59.2 |
| 1.4:1* | 40.4 | 67.4 |

*Phosphoric acid

Example 11

This example describes the conversion of ammonium 3-hydroxypropionate to butyl acrylate.

A mixture of ammonium 3-hydroxypropionate with a solvent composed of tricapryl amine/n-butanol (1:1) was heated to 160° C. for 3 hours. The reaction mixture was mainly butyl acrylate with small amounts of acrylic acid, and butyl 3-hydroxypropionate. The esters were easily separated from tricapryl amine by conventional fractional distillation.

Example 12

This example describes the conversion of the calcium salt of 3-hydroxypropionic acid to butyl acrylate.

The calcium salt of 3-hydroxypropionate was prepared from 3-HP and Ca(OH)$_2$. The calcium salt solution was subjected to extraction using an amount of sulfuric acid to neutralize the calcium salt to the free acid and using tricapryl amine as the solvent extractant. The extractant phase was separated from the aqueous phase. Butanol was added to the 3-HP-laden extraction solvent and the mixture was heated to cause esterification and dehydration, yielding butyl acrylate.

Example 13

This example describes a one-pot synthesis of butyl acrylate from 3-HP using an acid catalyst.

10.0 g of 30% 3-HP, 100 ml of n-butanol and 5 drops of conc. H$_2$SO$_4$ were mixed in a 250 ml flask. The mixture was refluxed with a Dean-Stark trap attached to remove the water. The refluxing was continued until no more water was collecting in the Dean-Stark trap. A distillation apparatus was attached and most of the n-butanol was distilled off. Next, the temperature was reduced and a vacuum applied (0.5 torr, 80° C.) to distill the remaining liquid. 1.58 g of butyl acrylate was obtained, along with some butanol. The yield of butyl acrylate was 37%.

Example 14

This example describes the preparation of 3-alkoxypropionate esters using basic catalysts.

5.12 g of 30% 3-HP aqueous solution, 0.50 g of Mg(OH)$_2$, and 53.58 g of butanol were added to a 600 ml autoclave Parr reactor. The resulting mixture was flushed with 50 psi of nitrogen gas three times to remove air, after which the reactor was heated to 220° C. for 1.6 hours. At the conclusion of the heating period, the reactor was cooled to room temperature and de-pressurized. The reactor contents were centrifuged to separate solids from the solution. After removing the solids, the solution was analyzed by gas chromatography for butyl 3-butoxypropionate ester, butyl 3-hydroxypropionate, and butyl acrylate. The yield of butyl 3-butoxypropionate ester was 48%, the yield of butyl 3-hydroxypropionate was 5%, and the yield of butyl acrylate was 47%.

The process was repeated by substituting Ca(OH)$_2$ and NaOH for the Mg(OH)$_2$ catalyst. The yields of butyl 3-butoxypropionate ester varied depending upon the identity of the catalyst, with the order being Mg>Ca>Na.

The process was repeated by substituting ethanol for butanol. The reaction provided yields of ethyl 3-ethoxypropionate ester ranging from 5 to 50% depending on the alkaline earth metal salt, with the order being Mg>Ca>Na.

Example 15

This example describes an alternative preparation of 3-alkoxypropionate esters using basic catalysts.

Butyl acrylate, prepared according to Example 10, was converted to butyl 3-butoxypropionate ester by reacting it with calcium hydroxide and butanol at about 50° C.

Example 16

This example describes the preparation of various alkyl acrylate esters by dehydrating 3-HP esters using various catalysts.

A catalyst was placed in a 3-neck flask that was equipped with a temperature probe (in contact with the catalyst). A distillation column and receiving flask were attached so that the vapors formed during the reaction could be collected, and the catalyst was heated to the desired temperature. A solution of a 3-hydroxypropionic acid ester in the corresponding alcohol was added drop-wise directly onto the catalyst using a syringe. The liquid that distilled over was collected and analyzed by gas chromatography. The results, and corresponding experimental conditions are shown in the following table.

| Ester | Catalyst | Temperature (° C.) | Concentration of Ester in Solvent (%) | Solvent | Yield of Acrylic ester (GC) (%) | Yield of Acrylic acid (GC) (%) |
|---|---|---|---|---|---|---|
| Ethyl | NaH$_2$PO$_4$-Silica | 275 | — | EtOH | 49 | 26 |
| Ethyl | NaH$_2$PO$_4$-Silica | 250 | 35 | EtOH | 53 | — |
| Ethyl | NaH$_2$PO$_4$-Silica | 250 | 50 | EtOH | 14 | 21 |
| Ethyl | NaH$_2$PO$_4$-Silica | 180 | 40 | EtOH | 30 | — |
| Ethyl | Copper-H$_3$PO$_4$ | 220 | 20 | EtOH | 50 | 50 |
| Methyl | NaH$_2$PO$_4$-Silica | 280 | — | MeOH | 78 | — |
| Methyl | CuSO$_4$-Silica | 280 | — | MeOH | 37 | 9 |
| Methyl | Cs$_2$CO$_3$-Silica | 220 | 45 | MeOH | 49 | — |
| Butyl | NaH$_2$PO$_4$-Silica | 280 | 50 | BuOH | 40 | — |

Similar dehydration reactions were performed using 3-HP as the starting material and a flask containing heated catalyst in place of the GC:

(a) Aqueous 3-HP was dehydrated to acrylic acid over NaH$_2$PO$_4$-Silica gel catalyst at 180° C. Based on GC and HPLC analysis, the yield of acrylic acid was 90-96%.

(b) Aqueous 3-HP was dehydrated to acrylic acid over H$_3$PO$_4$-Silica gel catalyst at 180° C. Based on GC and HPLC analysis, the yield of acrylic acid was 85-90%.

(c) Aqueous 3-HP was dehydrated to acrylic acid over CuSO$_4$-Silica gel catalyst at 180° C. Based on GC and HPLC analysis, the yield of acrylic acid was 73%.

(d) Aqueous 3-HP was dehydrated to acrylic acid over Zeolite H-β powder and 85% H$_3$PO$_4$ as the catalyst at 180° C. Based on GC and HPLC analysis, the yield of acrylic acid was 71%.

(e) Aqueous 3-hydroxyisobutyric acid was dehydrated to methacrylic acid over NaH$_2$PO$_4$-Silica gel catalyst at 270° C. Based on GC analysis, the yield of methacrylic acid was 79%.

Example 17

This example describes the preparation of the methyl ester of 3-HP in an amide solvent using Amberlyst-15 resin catalyst.

3-HP having a purity of about 70% was used as the starting material. To 25.02 g of 10.79% 3-HP in 1-octyl-2-pyrrolidinone was added 14.85 g methanol. The solution was refluxed at 76-78° C. in the presence of 1.26 g of Amberlyst-15 resin for 22 hours in a round bottom flask. GC analysis of the product showed that the reaction produced 3-HP methyl ester in a 76% yield.

Example 18

This example describes the preparation of the methyl ester of 3-HP in tributyl phosphate (TBP) solvent using Amberlyst-15 resin catalyst.

3-HP having a purity of about 70% was used as the starting material. To 18 g of 8.23% 3-HP in TBP was added 30.19 g methanol. The solution was refluxed at 70° C. in to the presence of 1.80 g of Amberlyst-15 resin for 17 hours in a round bottom flask. GC analysis of the product showed that the reaction produced 3-HP methyl ester in a 75.5% yield.

Example 19

This example describes the preparation of the methyl ester of 3-HP in an amide solvent using $H_2SO_4$ catalyst.

3-HP having a purity of about 70% was used as the starting material. To 12.03 g of 22.9% 3-HP in 1-octyl-2-pyrrolidinone was added 2.91 g methanol and 0.13 g $H_2SO_4$ (98%). The solution was refluxed at 83° C. for 2 hours in a round bottom flask. GC analysis of the product showed that the reaction produced 3-HP methyl ester in a 67.5% yield.

Example 20

This example describes the preparation of the methyl ester of 3-HP in an amide solvent using Amberlyst-15 resin as the catalyst.

3-HP having a purity of about 99% was used as the starting material. To 12.02 g of 9.7% 3-HP in 1-octyl-2-pyrrolidinone was added 6.24 g methanol. The solution was refluxed at 71° C. in the presence of Amberlyst-15 resin for 21 hours in a round bottom flask. GC analysis of the product showed that the reaction produced 3-HP methyl ester in a 99.1% yield.

A number of embodiments of the invention have been described. Nevertheless, it will be understood that various modifications may be made without departing from the spirit and scope of the invention. Accordingly, other embodiments are within the scope of the following claims.

What is claimed is:

1. A method for preparing acrylic acid, comprising: (a) providing a fermentation broth comprising 3-hydroxypropionic acid; (b) forming an aqueous solution comprising the 3-hydroxypropionic acid, from the fermentation broth; and (c) heating the aqueous solution to vaporize the 3-hydroxypropionic acid and to dehydrate the 3-hydroxypropionic acid in a vapor phase reaction in the presence of an acid dehydration catalyst to form acrylic acid; wherein a yield of acrylic acid from dehydrating 3-hydroxypropionic acid is at least 66%.

2. A method according to claim 1 wherein the acid dehydration catalyst is selected from the group consisting of $NaH_2PO_4$-silica gel, $H_3PO_4$-silica gel, $CuSO_4$-silica gel, and zeolite H-β-$H_3PO_4$.

3. The method according to claim 1, wherein the yield of acrylic acid from dehydrated 3-hydroxypropionic acid is at least 75%.

4. The method according to claim 1, wherein the yield of acrylic acid from dehydrated 3-hydroxypropionic acid is at least 81%.

5. The method according to claim 1, wherein the yield of acrylic acid from dehydrated 3-hydroxypropionic acid is at least 94%.

6. A method for preparing acrylic acid, comprising: (a) providing a fermentation broth comprising 3-hydroxypropionic acid; (b) forming an aqueous solution comprising the 3-hydroxypropionic acid from the fermentation broth; (c) heating and vaporizing the aqueous solution comprising the 3-hydroxypropionic acid; and (d) dehydrating the 3-hydroxypropionic acid to acrylic acid by a vapor phase reaction in the presence of an acid dehydration catalyst; wherein a yield of acrylic acid from 3-hydroxypropionic acid is at least 66%.

7. A method according to claim 6 wherein the acid dehydration catalyst is selected from the group consisting of $NaH_2PO_4$-silica gel, $H_3PO_4$-silica gel, $CuSO_4$-silica gel, and zeolite H-β-$H_3PO_4$.

8. The method according to claim 6, wherein the yield of acrylic acid from dehydrated 3-hydroxypropionic acid is at least 78%.

9. The method according to claim 6, wherein the yield of acrylic acid from dehydrated 3-hydroxypropionic acid is at least 81%.

10. The method according to claim 6, wherein the yield of acrylic acid from dehydrated 3-hydroxypropionic acid is at least 94%.

11. A method for preparing acrylic acid, comprising: (a) providing an aqueous solution comprising 3-hydroxypropionic acid; (b) heating the aqueous solution to vaporize the 3-hydroxypropionic acid; and (c) converting the 3-hydroxypropionic acid to acrylic acid by a vapor phase reaction in the presence of an acid dehydration catalyst; wherein a yield of acrylic acid from dehydrating 3-hydroxypropionic acid is at least 66%.

12. A method according to claim 11 wherein the dehydration catalyst is selected from the group consisting of $NaH_2PO_4$-silica gel, $H_3PO_4$-silica gel, $CuSO_4$-silica gel, and zeolite H-β-$H_3PO_4$.

13. The method according to claim 11, wherein the yield of acrylic acid from dehydrated 3-hydroxypropionic acid is at least 78%.

14. The method according to claim 11, wherein the yield of acrylic acid from dehydrated 3-hydroxypropionic acid is at least 81%.

15. The method according to claim 11, wherein the yield of acrylic acid from dehydrated 3-hydroxypropionic acid is at least 94%.

16. A method for preparing acrylic acid, comprising: (a) providing an aqueous solution comprising 3-hydroxypropionic acid, wherein providing the aqueous solution comprises extracting the 3-hydroxypropionic acid from a fermentation broth with a basic amine to provide the aqueous solution; (b) heating the aqueous solution to vaporize the 3-hydroxypropionic acid; and (c) converting the 3-hydroxypropionic acid to acrylic acid by a vapor phase reaction in the presence of an acid dehydration catalyst; wherein a yield of acrylic acid from dehydrating 3-hydroxypropionic acid is at least 66%.

17. The method according to claim 16 wherein the basic amine is tricapryl amine, tridecylamine, or tridodecyl amine.

18. The method according to claim 16, wherein the yield of acrylic acid from dehydrated 3-hydroxypropionic acid is at least 75%.

19. The method according to claim 16, wherein the yield of acrylic acid from dehydrated 3-hydroxypropionic acid is at least 81%.

20. The method according to claim 16, wherein the yield of acrylic acid from dehydrated 3-hydroxypropionic acid is at least 94%.

21. The method of claim 16, wherein the acid dehydration catalyst is selected from the group consisting of $NaH_2PO_4$-silica gel, $H_3PO_4$-silica gel, $CuSO_4$-silica gel and zeolite H-β-$H_3PO_4$.

* * * * *

UNITED STATES PATENT AND TRADEMARK OFFICE
CERTIFICATE OF CORRECTION

PATENT NO.         : 8,846,353 B2                                   Page 1 of 1
APPLICATION NO.    : 13/719095
DATED              : September 30, 2014
INVENTOR(S)        : Paraskevas Tsobanakis et al.

It is certified that error appears in the above-identified patent and that said Letters Patent is hereby corrected as shown below:

In the Claims

In column 12, line 17, in claim 8, delete "78%." and insert -- 75%. --, therefor.

In column 12, line 39, in claim 13, delete "78%." and insert -- 75%. --, therefor.

Signed and Sealed this
Third Day of March, 2015

Michelle K. Lee
*Deputy Director of the United States Patent and Trademark Office*